US006773397B2

(12) United States Patent
Kelly (10) Patent No.: US 6,773,397 B2
(45) Date of Patent: Aug. 10, 2004

(54) SYSTEM FOR PROCESSING SIGNAL DATA REPRESENTING PHYSIOLOGICAL PARAMETERS

(75) Inventor: Clifford Mark Kelly, Windham, NH (US)

(73) Assignee: Draeger Medical Systems, Inc., Danvers, MA (US)

( * ) Notice: Subject to any disclaimer, the term of this patent is extended or adjusted under 35 U.S.C. 154(b) by 0 days.

(21) Appl. No.: 10/247,424

(22) Filed: Sep. 19, 2002

(65) Prior Publication Data

US 2003/0088184 A1 May 8, 2003

Related U.S. Application Data

(60) Provisional application No. 60/328,619, filed on Oct. 11, 2001.

(51) Int. Cl.$^7$ ................................................. A61B 5/00
(52) U.S. Cl. ........................ 600/301; 600/323; 600/481; 600/529
(58) Field of Search ............................... 600/300–301, 600/323, 324, 481, 485, 500–504, 508, 509, 528, 529, 544–546, 549

(56) References Cited

U.S. PATENT DOCUMENTS

| 4,023,563 A | 5/1977 | Reynolds et al. |
| 4,027,663 A | 6/1977 | Fischler et al. |
| 4,137,908 A | 2/1979 | Degonde et al. |
| 4,459,993 A | 7/1984 | Foreman |
| 4,549,551 A | 10/1985 | Dyck et al. |

(List continued on next page.)

OTHER PUBLICATIONS

Hambly, Peter Dr., "Measuring The Blood Pressure", Issue 11, 2002, Article 6, download from http://www.nda.ox-.ac.uk/wfsa/html/u11/u1106_01.htm on Feb. 15, 2002. ©World Federation of Societies of Anaesthesiologists, WWW implementation by the NDA Web Team, Oxford. 3pgs.

"How Heart Rate Monitors Work", download from http://www.chponline.com/HRM2.htm on Feb. 27, 2002. 3pgs.

(List continued on next page.)

Primary Examiner—Mary Beth Jones
Assistant Examiner—Patricia C. Mallari
(74) Attorney, Agent, or Firm—Jack Schwartz & Associates (57) ABSTRACT

Determination of a physiological parameter value includes reception of several signals, each representing a respective one of several physiological parameters and including a pulsation associated with the parameter. A system detects a pulsation associated with a physiological parameter. The system includes an input device for receiving a plurality of different signals, each of the plurality of different signals indicating a pulsation in respective different physiological parameters. A signal processor detects and accumulates information from the plurality of different signals. The accumulated information including values of relative delay between the pulsation in the respective different parameters. A timing processor determines a timing of the pulsation in at least one of the different parameters based at least on the accumulated information. The physiological parameters include parameters associated with at least two of, non-invasive blood pressure, invasive blood pressure, heart beat, blood oxygen saturation level, respiration rate, an ECG and temperature.

13 Claims, 4 Drawing Sheets

U.S. PATENT DOCUMENTS

| | | | |
|---|---|---|---|
| 4,860,759 A | | 8/1989 | Kahn et al. |
| 5,033,472 A | * | 7/1991 | Sato et al. .................. 600/504 |
| 5,152,296 A | | 10/1992 | Simons |
| 5,392,781 A | * | 2/1995 | Phillipps et al. ............ 600/493 |
| 5,687,738 A | * | 11/1997 | Shapiro et al. ............. 600/528 |
| 5,749,831 A | * | 5/1998 | Baker ......................... 600/301 |
| 5,876,348 A | * | 3/1999 | Sugo et al. ................. 600/490 |
| 6,018,677 A | | 1/2000 | Vidrine et al. |
| 6,083,172 A | | 7/2000 | Baker, Jr. et al. |
| 6,178,343 B1 | | 1/2001 | Bindszus et al. |
| 6,183,417 B1 | | 2/2001 | Geheb et al. |
| 6,221,012 B1 | | 4/2001 | Maschke et al. |

OTHER PUBLICATIONS

Fearnley, SF Dr., "Pulse Oximetry", Issue 5, 1995, Article 2, download from http://www.nda.ox.ac.uk/wfsa/html/u05/u05_003.htm on Feb. 15, 2002. ©World Federation of Societies of Anaesthesiologists, WWW implementation by the NDA Web Team, Oxford. 3pgs.

International Search Report.

* cited by examiner

SYSTEM FOR PROCESSING SIGNAL DATA REPRESENTING PHYSIOLOGICAL PARAMETERS

CROSS REFERENCE TO RELATED APPLICATIONS

This application claims priority to Provisional Application Serial No. 60/328,619, filed Oct. 11, 2001 and entitled "A System for Detecting and Processing Signal Data Representing Repetitive Anatomical Functions."

TECHNICAL FIELD

The present invention relates to medical systems and in particular to systems for monitoring physiological parameters.

BACKGROUND

Patient treatment often includes monitoring of various physiological parameters. Conventionally, such monitoring begins by attaching sensors to several locations on a patient's body. The sensors transmit signals to one or more devices, which in turn determine the values of subject parameters based on the signals. In this regard, a particular parameter value may be determined based on a signal received from one or more of the attached sensors.

Many methods have been employed to determine parameter values based on sensed physiological signals. According to some of these methods, a beat detector detects a beat that is present in a signal associated with a particular parameter. The detected beat is then used to determine a value of the particular parameter. For example, conventional algorithms may be used to compute a maximum pressure or peak of an electrocardiogram (EKG) from a detected beat. Values of other physiological parameters may be determined based on beats that are present in signals associated with the other parameters. These parameters include non-invasive blood pressure (NIBP), invasive blood pressure (IBP), and blood oxygen saturation level (SPO2).

Conventional beat detectors operate best when signals corresponding to associated physiological parameters are free of noise. These beat detectors therefore have difficulty in properly identifying beats in the presence of environmental noise and/or patient movement. As a result, any parameter values determined based on the identified beats suffer from inaccuracies.

Some systems attempt to address the foregoing by gating a beat associated with one parameter using a beat associated with another parameter, or by using a beat detected for one parameter to filter a beat associated with another parameter. The unidirectional processing of these systems does not lend itself to accuracy or flexibility. Moreover, the algorithms used for gating and filtering reflect a wide margin of error due to variations in physiology among patients. Consequently, these systems do not provide satisfactory accuracy and reliability.

A system is therefore desired to improve the determination of pulsation-based parameter values that satisfactorily addresses signal noise induced by motion or other environmental sources.

SUMMARY

To address at least the foregoing, some aspects of the present invention provide a system, method, apparatus, and means to determine a value of a physiological parameter. A system detects a pulsation associated with a physiological parameter. The system includes an input device for receiving a plurality of different signals, each of the plurality of different signals indicating a pulsation in respective different physiological parameters. A signal processor detects and accumulates information from the plurality of different signals. The accumulated information including values of relative delay between the pulsation in the respective different parameters. A timing processor determines a timing of the pulsation in at least one of the different parameters based at least on the accumulated information. The physiological parameters include parameters associated with at least two of, non-invasive blood pressure, invasive blood pressure, heart beat, blood oxygen saturation level, respiration rate, an ECG and temperature.

The present invention is not limited to the disclosed embodiments, however, as those of ordinary skill in the art can readily adapt the teachings of the present invention to create other embodiments and applications.

BRIEF DESCRIPTION OF THE DRAWINGS

The exact nature of this invention, as well as its advantages, will become readily apparent from consideration of the following specification as illustrated in the accompanying drawings, wherein.

DETAILED DESCRIPTION

The following description is provided to enable any person of ordinary skill in the art to make and use the invention and sets forth the best modes contemplated by the inventor for carrying out the invention. Various modifications, however, will remain readily apparent to those in the art.

Figure 1:
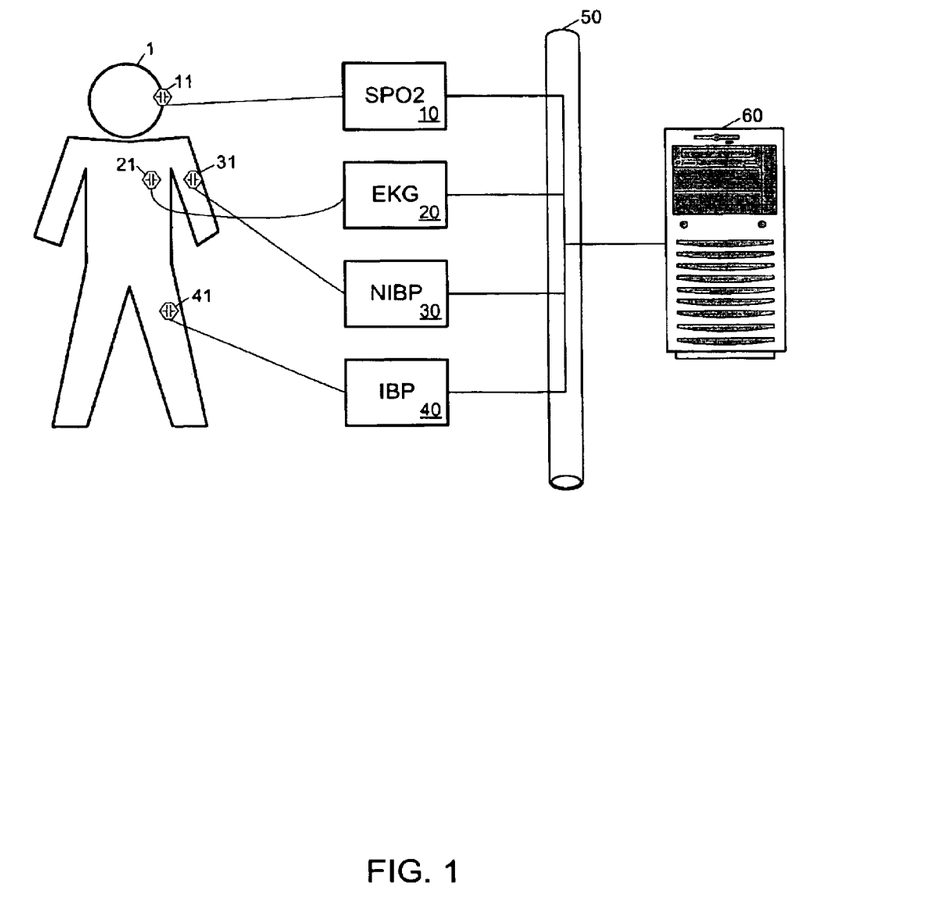
FIG. 1 is diagram illustrating patient monitoring according to some embodiments of the present invention.

FIG. 1 illustrates a patient monitoring system according to some embodiments of the present invention. The system illustrated in FIG. 1 may be located in any number of locations and may be used in any number of situations. Possible locations include a hospital, an office, and an ambulance, and possible situations include during an operation, during a checkup, and during a recovery period.

Attached to patient 1 are monitoring devices such as sensors for producing signals associated with physiological parameters. A physiological parameter according to some embodiments of the invention includes any identifiable characteristic of a patient's physiology. These parameters may include SPO2, NIBP, IBP, a heart beat associated parameter (e.g., HR—heart rate), respiration rate, and temperature.

According to some embodiments, the SPO2 parameter specifies a percentage of hemoglobin that is carrying oxygen. SPO2 values may be determined using pulse oximetry, in which blood (often located in the earlobe) is illuminated with two wavelengths of light and the SPO2 value is calculated based on the relative absorption of the two wavelengths. The NIBP and IBP parameters may specify blood pressures during heart contraction and during heart relaxation measured using a traditional blood pressure cuff (NIBP) or a cannula placed in an artery (IBP). Also in some embodiments, the HR parameter is a measure of heart beats over a time period, the respiration rate parameter is a measure of oxygen consumption over a period of time, and the temperature parameter reflects a core body temperature.

The signals produced by the sensors are received by monitoring devices such as monitors for determining a value of a physiological parameter therefrom. More specifically, SPO2 monitor 10 receives a signal associated with an SPO2 parameter from sensor 11, EKG monitor 20 receives a signal associated with an EKG parameter from sensor 21, NIBP monitor 30 receives a signal associated with an NIBP parameter from sensor 31, and IBP monitor 40 receives a signal associated with an IBP parameter from sensor 41. Each of sensors 11, 21, 31 and 41 is a sensor suitable to produce a signal representing an associated parameter. Accordingly, each monitor is used to determine a value of an associated parameter.

Monitors 10, 20, 30 and 40 may determine a value of a parameter based at least on a pulsation that is present in a signal associated with the parameter. In this regard, the pulsation is also considered to be associated with the signal. In some instances, the pulsation corresponds to the heart beat of patient 1, but it may also correspond to the pulse rate of patient 1. It should be noted that a pulsation according to the present invention may comprise any pulse represented in any signal. In some embodiments, a pulsation is associated with signals representing two or more physiological parameters and is used to determine the parameters.

It should be noted that, according to some embodiments, each monitor may receive signals from more than one sensor. Conversely, two or more monitors may receive signals from the same sensor. Each sensor may transmit a signal using any currently or hereafter-known system for transmitting data, including a RF, an infrared, and a fiber-optic system. Moreover, the signals may be transmitted over one or more of an IP network, an Ethernet network, a Bluetooth network, a cellular network, and any other suitable network.

Monitors 10, 20, 30 and 40 are in communication with communication bus 50. Again, communication bus 50 may comprise any type of network, and communication therewith may proceed in accordance with any hardware and/or software protocol such as TCP/IP protocol. Also in communication with communication bus 50 is mapping server 60. According to some embodiments, mapping server 60 receives signals from monitors 10, 20, 30 and 40. As described above, each of the signals is associated with a respective parameter. Mapping server 60 determines values for two or more parameters based at least on a pulsation associated with each of the two or more parameters. Mapping server 60 also determines a temporal relationship between the two or more pulsations. The relationship describes a relative time delay between the two or more pulsations and is stored in association with the determined values. In one example, sensor 11 and sensor 41 produce signals including a pulsation corresponding to a heart beat of patient 1. However, since sensor 41 is located farther from the heart than sensor 11, the pulsation in the signal produced by sensor 41 is delayed with respect to the pulsation in the signal produced by sensor 11. This and other processes will be described in more detail with respect to FIG. 2.

Figure 2:
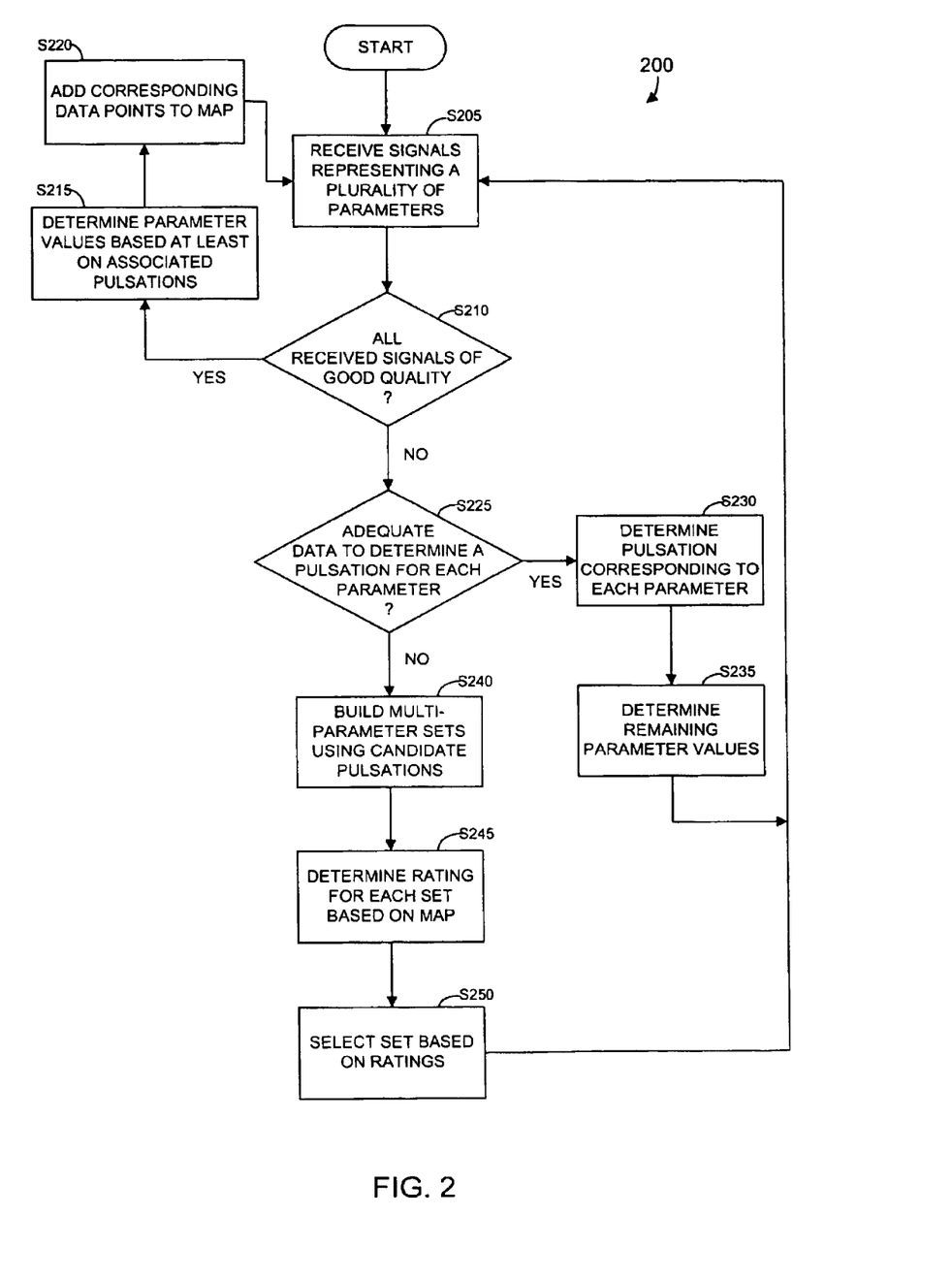
FIG. 2 is a flow diagram illustrating process steps according to some embodiments of the present invention.

In this regard, FIG. 2 is a flow diagram of process steps 200 according to some embodiments of the present invention. Hardware and/or software for executing process steps 200 may be located in and/or executed by one or more of sensors 11, 21, 31, and 41, monitors 10, 20, 30, and 40, and mapping server 60 of FIG. 1.

Turning to the specific steps, signals representing a plurality of physiological parameters are received in step S205. In the presently-described embodiment, the signals are received by mapping server 60 from monitors 10, 20, 30, and 40. More than one received signal may represent a single parameter, and a received signal may represent more than one parameter. Accordingly, a signal that represents a parameter is a signal that encodes at least some information that is useful for determining a value of the parameter.

Next, in step S210, it is determined whether all the received signals are of good quality. This determination may be based on a threshold noise tolerance, which may be equal or different for each received signal. In some embodiments of step S210, it is determined whether enough of the received signals are of good quality to accurately determine values for each represented parameter. If the received signals are of good quality, values of associated parameters are determined in step S215.

As described above, the value of a parameter is determined based on at least a pulsation associated with the parameter. Accordingly, in step S215, pulsations respectively associated with two or more parameters are determined based on the received signals and a value of each of the two or more parameters is determined based on an associated pulsation. The determined parameter values may be presented to an operator by appropriate ones of monitors 10, 20, 30 and 40 or by mapping server 60.

In one example of step S215, pulsations associated with the NIBP parameter, the IBP parameter, and the SPO2 parameter are determined based on signals received from sensor 30, sensor 40 and sensor 10, respectively. This determination may proceed using any currently or hereafter-known pulse detector, and results in, among other information, a time of occurrence corresponding to each pulsation. In this example, the pulsation associated with the HR parameter is determined to have occurred 2 milliseconds after the pulsation associated with the IBP parameter and 4 milliseconds after the pulsation associated with the NIBP parameter. Based on the respective pulsations, also determined in step S215 are an NIBP value of 110/80, an IBP value of 120/90, and an SPO2 value of 97%.

Data points corresponding to the determined pulsations and values are added to a map or other data structure in step S220. The map specifies temporal relationships between pulsations associated with two or more physiological parameters for several combinations of parameter values. According to the above example, a combination of the three determined parameter values (i.e. 110/80, 120/90 and 77) is stored in a map along with an indication of a temporal relationship, or time delay, between the pulsations associated with two of the parameters (i.e. 2 ms, 4 ms or 6 ms).

Figure 3A:
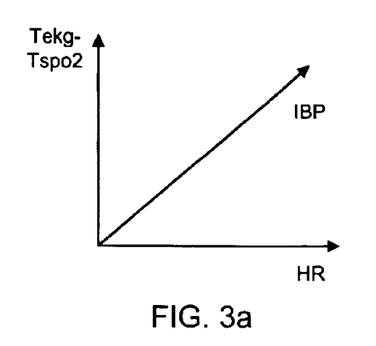
FIGS. 3a through 3f comprise diagrams illustrating map domains used in conjunction with some embodiments of the present invention.
Figure 3B:
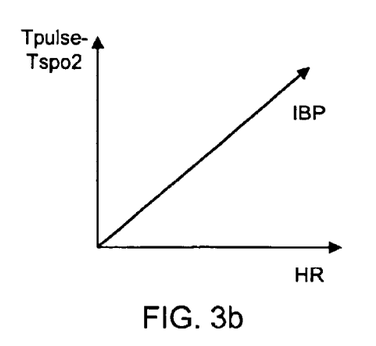
Figure 3C:
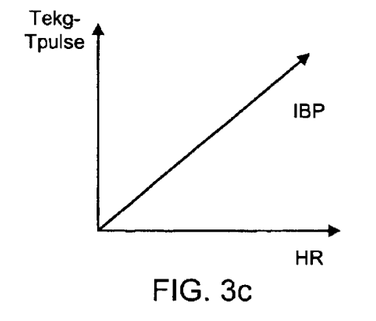
Figure 3D:
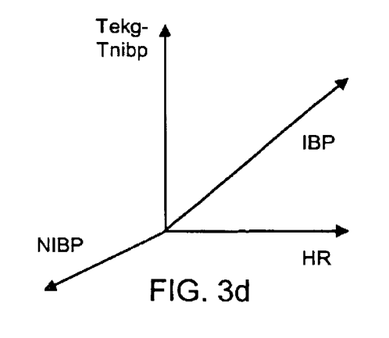

FIGS. 3a through 3f illustrate map domains to which data points are added in step S220 of FIG. 2 according to some embodiments of the present invention. As shown, each domain allows a temporal relationship between two pulsations associated with two physiological parameters to be expressed as a function of two or more physiological parameters. More specifically, FIG. 3a illustrates a domain used to map a temporal relationship between an EKG pulsation and an SPO2 pulsation as a function of a combination of IBP and HR values. In another example, the FIG. 3d domain allows mapping of a temporal relationship between an EKG pulsation and an NIBP pulsation as a function of IBP, HR and NIBP values. It should therefore be noted that a data point added to a map in step S220 may associate values of any number of parameters with a temporal relationship between pulsations, and that the values may represent neither, one, or all of the parameters associated with the pulsations.

A map used in conjunction with some embodiments of the invention comprises a data structure that associates a plurality of sets of pulsation-based physiological parameter values with data representing a temporal relationship between a plurality of pulsations associated with respective ones of a plurality of parameters. In some embodiments, conventional curve-fitting algorithms are used to determine a map comprising one or more equations that approximate the data points determined in step S215. Such equations may present a temporal relationship in terms of a combination of parameter values. For example, an equation approximating a map according to FIG. 3d may be in the form $(T_{ekg}-T_{nibp})=Fxn(HR, IBP, NIBP)$ These equations may be periodically revised based on the addition of data points in step S220.

After addition of a data point to an appropriate map in step S220, flow returns to step S205 and continues as described above. Accordingly, data points continue to be added to maps in step S220 as long as suitable good-quality signals are received in step S205.

Flow continues to step S225 from step S210 in a case that it is determined that one or more required signals are not of sufficient quality. In step S225, it is determined whether the received signals provide enough good-quality data to determine a pulsation associated with each parameter of interest. If so, flow proceeds to step S230, wherein pulsations respectively associated with each parameter of interest are determined.

In some embodiments, the pulsations are determined by first determining pulsations associated with one or more parameters based on good-quality signal data and using any currently or hereafter-known pulse detector. Each of these one or more parameters is then determined using the associated pulsation, data from the received signals, and currently or hereafter-known algorithms for determining the parameter. Since good-quality signal data is not available to determine pulsations of each parameter of interest, pulsations associated with one or more parameters of interest will not be determined. In order to determine one of these pulsations, a temporal relationship between the one pulsation and one or more of the determined pulsations is initially determined.

Figure 3E:
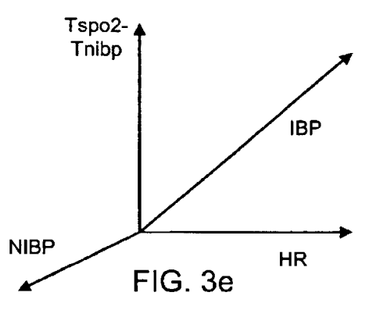
Figure 3F:
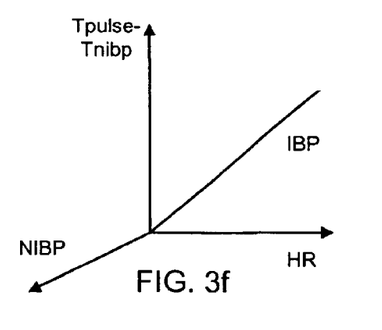

The temporal relationship may be determined based on the map created in step S220. In this regard, the map (function, data structure) is usable to determine a temporal relationship between a determined pulsation and an undetermined pulsation based on a combination of two or more determined parameter values. For example, pulsations and values associated with HR, NIBP and IBP were determined in step S230 based on good-quality signals, but no pulsation was determined for SPO2. Accordingly, data points populating the map of FIG. 3e are used in step S230 to determine a temporal relationship between the SPO2 pulsation and the pulsation associated with NIBP based on the HR, NIBP and IBP parameter values. Particularly, a point on the map is identified for which the values of HR, NIBP and IBP are identical to the values determined in step S230. The temporal relationship $(T_{spo2}-T_{nibp})$ corresponding to the identified point is then determined. Since $T_{nibp}$ is known, $T_{spo2}$ can be determined from the temporal relationship. $T_{spo2}$ is then used as described above to determine a value of the SPO2 parameter.

It should be noted that the data points populating the map used in step S230 may include those identified in step S220 as well as those derived from different sources. In one example, pre-existing data records associated with patient 1 may include data points that can be used to populate maps such as those shown in FIGS. 3a through 3f. More specifically, data points may be appended to a patient record each time patient 1 is monitored, and the data points may be used to determine temporal relationships as described above. In some embodiments, the appended data points are those determined based on signals that exceed a predetermined quality threshold.

Of course, many other methods for determining a pulsation in step S230 may be used in conjunction with the present invention. In some embodiments, several temporal relationships between known pulsations and an undetermined pulsation are determined based on different mappings as described above. The several temporal relationships may be averaged or otherwise weighted (perhaps based on relative signal qualities) to determine a single temporal relationship that is thereafter used to determine the pulsation.

After determination of the pulsations, any parameter values that have not yet been determined are determined based on the pulsations in step S235. This determination may proceed using algorithms as described above. All the parameters determined in steps S230 and S235 may then be presented to an operator, stored and/or used to trigger other processes. Flow returns to step S205 from step S235.

If the determination of step S225 is negative, multi-parameter sets are built in step S240 using candidate pulsations. According to some embodiments of step S225, multi-parameter sets are built as follows. First, for each parameter to be determined, an associated pulsation is determined based on an associated received signal as described above. A value is determined for each parameter based on an associated pulsation, also as described above. The determined values comprise a multi-parameter set. It should be noted that since each received signal is of poor quality, the pulsations and parameters determined therefrom are unreliable.

Next, a second set of associated pulsations, one for each parameter, is determined based on the received signals. A second set of parameter values is then determined based on the second set of associated pulsations. Additional sets of parameter values may be similarly generated. Therefore, these embodiments result in multiple sets of parameter values, with each set corresponding to a set of pulsations determined based on noisy signals.

Next, in step S245, a rating is determined for each set of parameter values based on the mapping, which comprises temporal relationships determined for each of two or more combinations of parameter values. The rating for a set of parameter values may be determined by using currently or hereafter-known systems for determining how closely a data point matches a set of data points. In these embodiments, the rating reflects how closely a set of parameter values and associated pulsations conforms to the mapping (or mappings) created in step S220. A set of parameter values is then selected in step S250 based at least on the determined ratings. For example, the set selected in step S250 may be the set of values that is associated with a rating indicating that the set approximates the mapping more closely than any other set determined in step S240. Flow thereafter returns to step S205.

Figure 4:
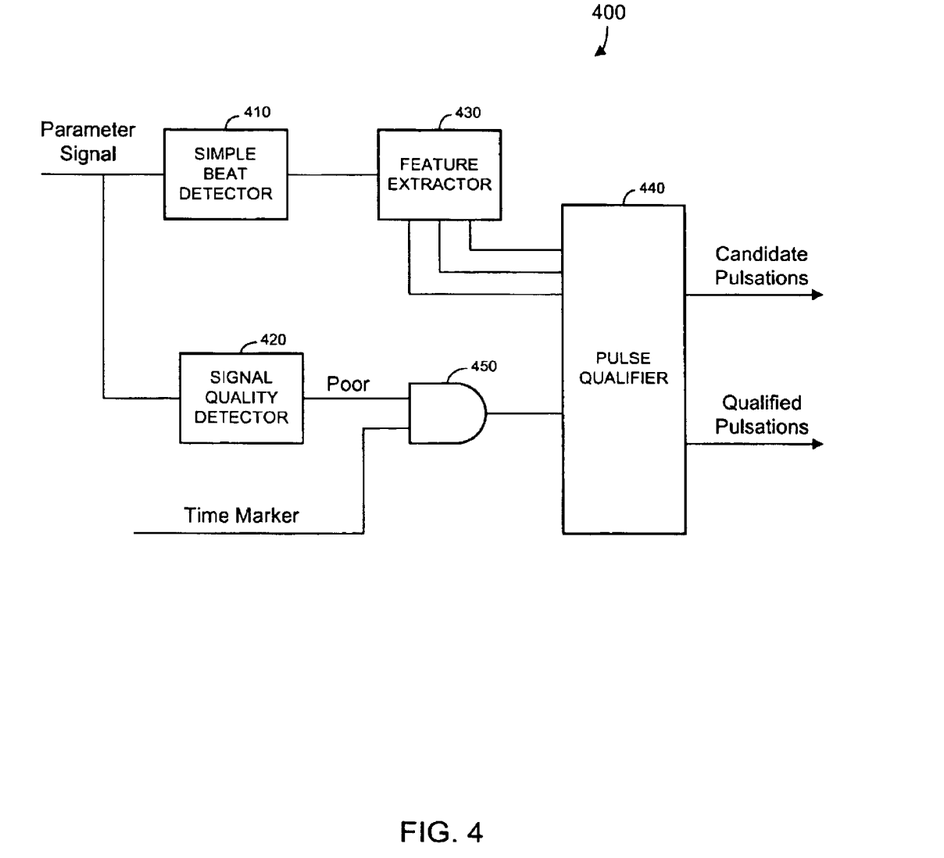
FIG. 4 is a block diagram of a single parameter beat detector according to some embodiments of the present invention.

FIG. 4 is a block diagram of single parameter beat detector 400 that is used in some implementations of process steps 200. In some embodiments, one detector such as beat detector 400 is associated with each parameter of interest. In this regard, each of monitors 10, 20, 30 and 40 may comprise one such detector. Therefore, in a case that beat detector 400 is associated with the SPO2 parameter, the parameter signal received by simple beat detector 410 and signal quality detector 420 is received from sensor 11.

Simple beat detector 410 detects a pulsation in the received signal. Features are then extracted from the detected pulsation by feature extractor 430 to better determine the timing and shape of the pulsation. These features may include an amplitude in a rectified and filtered domain, timing information, and pulse shape data. It should be noted that the above functions of elements 410 and 430 may be performed using currently or hereafter-known beat detection techniques.

If the received signal is of good quality, the output of signal quality detector 420 is low, thereby causing AND gate 450 to output a low signal. Pulse qualifier 440 is designed so that, upon receiving a low output from gate 450, a qualified pulsation is determined and output in step S215 based on the features extracted by feature extractor 430. In this regard, the determination of a pulsation based on extracted features is known to those skilled in the art.

If a poor-quality signal is received, the output of signal quality detector is high and a Time Marker signal is input to pulse qualifier 440. The Time Marker signal indicates an expected timing of the pulsation associated with the parameter of beat detector 400. The expected timing is determined as described above with respect to step S230 based on a map and on the determined pulsations and values associated with other parameters. Accordingly, the Time Marker signal may be received from any system having access to the map and capable of determining the pulsations and associated parameter values. In this regard, such a system may receive the features extracted by each instantiation of feature extractor 430 in order to calculate the parameter values.

Therefore, in the case of a poor-quality signal, pulse qualifier 440 also uses the Time Marker signal in addition to the extracted features in order to determine a qualified pulsation. In some embodiments, the qualified pulsation is biased toward an expected timing represented by the Time Marker signal. Next, in step S235, a parameter value is determined based on the qualified pulsation.

In a case that sufficient good-quality signals are not available to determine an expected timing of an associated pulsation from the map, a special Time Marker signal is transmitted to gate 450. Upon detecting the special Time Marker signal, pulse qualifier 440 determines pulsations based on the extracted features and transmits the pulsations as candidate pulsations rather than as qualified pulsations. The candidate pulsations are used as described with respect to step S240 to build multi-parameter sets of values.

Those in the art will appreciate that various adaptations and modifications of the above-described embodiments can be configured without departing from the scope and spirit of the invention. In some embodiments, functions attributed above to monitors 10, 20, 30 and 40 are performed by a single monitoring unit, such as the Siemens Infinity Patient Monitoring System. Some embodiments also include the functions of mapping server 60 into the single monitoring unit. Moreover, embodiments of the present invention may differ from the description of process steps 200. Particularly, the particular arrangement of process steps 200 is not meant to imply a fixed order to the steps; embodiments of the present invention can be practiced in any order that is practicable.

Therefore, it is to be understood that, within the scope of the appended claims, the invention may be practiced other than as specifically described herein.

What is claimed:

1. A system for detecting a pulsation associated with a physiological parameter, comprising:
    an input device for receiving a plurality of different signals, each of the plurality of different signals indicating a pulsation in respective different physiological parameters;
    a signal processor for detecting and accumulating information from the plurality of different signals, the information including values of relative delay between pulsations in the respective different parameters; and
    a timing processor for determining a timing of the pulsation in at least one of the different parameters based at least on the accumulated information; wherein
    the plurality of different signals comprises at least two of (a) an electrocardiogram signal, (b) a blood oxygen saturation representative signal, (c) an invasive blood pressure representative signal, and (d) a non-invasive blood pressure representative signal.

2. A system according to claim 1, wherein
    the physiological parameters comprise parameter associated with at least two of non-invasive blood pressure, invasive blood pressure, heart beat, blood oxygen saturation level, respiration rate, an ECG (ElectroCardioGraph) and temperature.

3. A system for detecting a pulsation associated with a physiological parameter, comprising:
    an input device for receiving a plurality of different signals, each of the plurality of different signals indicating a pulsation in respective different physiological parameters;
    a signal processor for detecting and accumulating information from the plurality of different signals, the information including values of relative delay between the pulsation in the respective different parameters; and
    a timing processor for determining a timing of the pulsation in at least one of the
    different parameters based at least on the accumulated information and on information derived from different sources, wherein the signal processor appends information from patient monitoring sources to a patent record in response to patient admission and stores the appended information for future use and the signal processor appends information from patient monitoring sources to a patient record when the plurality of different signals are determined to exceed a predetermined quality threshold.

4. A system for detecting a pulsation associated with a physiological parameter, comprising:
    an input device for receiving a plurality of different signals, each of the plurality of different signals indicating a pulsation in respective different physiological parameters;
    a signal processor for detecting and accumulating information from the plurality of different signals, the information including values of relative delay between pulsations in the respective different parameters; and
    a timing processor for determining a timing of the pulsation in at least one of the different parameters based at least on the accumulated information and on information derived from different sources,
    the signal processor appends information from patient monitoring sources to a patient record when the plurality of different signals are determined to exceed a predetermined quality threshold.

5. A system according to claim 4, wherein
the signal processor appends information from patient monitoring sources to a patient record in response to patient admission and stores the appended information for future use.

6. A method for determining a value of a physiological parameter, comprising:
receiving a plurality of signals, each of said plurality of signals representing a respective one of a plurality of physiological parameters and comprising a pulsation associated with a corresponding parameter of said plurality of physiological parameters; and
determining, for each of a plurality of combinations of parameters for a particular patient, a temporal relationship between corresponding pulsations associated with different parameters of said plurality of combinations of parameters, said plurality of combinations of parameters comprising a heart beat associated parameter in combination with a parameter associated with at least one of, (a) non-invasive blood pressure, (b) invasive blood pressure, (c) blood oxygen saturation level and (d) respiration rate.

7. A method according to claim 6, wherein said plurality of combinations of parameters comprise a heart beat associated parameter in combination with a parameter associated with at least one of, (i) a cardiac ultrasound pulsation, (ii) temperature and (iii) an ECG.

8. A method according to claim 6, wherein said step of determining said temporal relationship between said corresponding pulsations comprises:
detecting and accumulating information from said plurality of different signals, said information including values of relative delay between corresponding pulsations associated with said different parameters of said plurality of combinations of parameters, and
determining a timing of a pulsation in at least one of said different parameters based at least on said accumulated information.

9. A method according to claim 6, further comprising:
Identifying and indicating when said plurality of different signals representing said plurality of combinations of parameters are determined to exceed a predetermined quality threshold.

10. A method for determining a value of a physiological parameter, comprising:
receiving a signal representing a first parameter of a plurality of physiological parameters;
receiving at least one signal respectively representing at least one other of the plurality of physiological parameters;
determining at least one value respectively associated with the first parameter;
determining values of a plurality of the at least one other of the physiological parameters based on the received at least one signal;
identifying a combination of values based on the determined values;
identifying a temporal relationship associated with the identified combination of values; and
determining a pulsation associated with the signal representing the first parameter based at least on the determined temporal relationship;
determining ratings corresponding to values representing said plurality of physiological parameters, and
selecting at least one parameter value based at least on said determined ratings.

11. A method according to claim 10, wherein
said step of determining at least one value and said step of determining values, both determine values associated with pulsation.

12. A device comprising a memory storing processor-executable process steps and a processor in communication with the memory and operative in conjunction with the stored process steps to perform the steps of claim 10.

13. A method according to claim 10, wherein
said combination of values comprise a heart beat associated value in combination with a value associated with at least one of, (a) non-invasive blood pressure, (b) blood oxygen saturation level, (c) respiration rate (d) a cardiac ultrasound pulsation, (e) an ECG and (e) temperature.

* * * * *